United States Patent [19]

Gondel et al.

[11] Patent Number: 5,209,829

[45] Date of Patent: May 11, 1993

[54] ACID ETCHING BATH FOR TITANIUM ALLOY OF COMPONENTS

[75] Inventors: Claude G. G. Gondel, Beaumont sur Oise; Christian P. H. G. Hennebelle, Paris, both of France

[73] Assignee: Societe Nationale d'Etude et de Construction de Moteurs d'Aviation "S.N.E.C.M.A.", Paris, France

[21] Appl. No.: 894,564

[22] Filed: Jun. 5, 1992

[30] Foreign Application Priority Data

Jun. 12, 1991 [FR] France .................. 91 07148

[51] Int. Cl.$^5$ .............................................. C25F 3/08
[52] U.S. Cl. ............................................... 204/129.75
[58] Field of Search ................................. 204/129.75

[56] References Cited

FOREIGN PATENT DOCUMENTS 62-86196 4/1987 Japan .

Primary Examiner—T. M. Tufariello
Attorney, Agent, or Firm—Oblon, Spivak, McClelland, Maier & Neustadt

[57] ABSTRACT

An acid etching bath for activating titanium alloy components, especially turbo-machine blades and discs, before macrographic anodic oxidation in an electrochemical etching process, known as the "blue-etch" process, for the non-destructive checking of the components, comprises 75±5 ml/1 of sulphuric acid, from 11 to 15 g/1 of sodium fluoride, and water as the balance.

4 Claims, No Drawings

ACID ETCHING BATH FOR TITANIUM ALLOY OF COMPONENTS

FIELD OF THE INVENTION

The invention relates to an acid etching bath for activating titanium alloys before macrographic anodic oxidation in an electro-chemical etching process comprising, in succession, the steps of degreasing, rinsing, activation by acid etching, rinsing, anodic oxidation in a trisodium phosphate bath, rinsing, and development by etching in a nitrohydrofluoric bath.

BACKGROUND OF THE INVENTION

The operating conditions of turbo-engines, especially aircraft engines, have led to the utilization of numerous titanium or titanium alloy components in such engines. It is important that these components should be subjected to a non-destructive checking capable of revealing the various defects from which they may suffer. In particular, they should be examined for possible manufacturing defects such as segregations, inclusions, porosity, etc., transformation defects such as cracks, incrustations, heterogeneity, contaminations, etc., and machining or polishing defects such as work-hardening, local overheating, etc. For this purpose, there is in existence an electro-chemical etching process which is well known in the art as the "blue-etch process".

This electro-chemical etching process consists, generally, in carrying out the following operations on the component to be checked:

1. Conventional degreasing by immersion in an alkaline bath;
2. Rinsing with cold water in a tank of running water, or by sprinkling;
3. Possible removal of a work-hardened layer, about 5 microns, by fluo nitric etching;
4. Rinsing with cold water in a tank of running water;
5. Chemical activation by immersion in an acid salt bath for etching with a macrographic effect;
6. Rinsing with cold water in a tank of running water;
7. Anodic oxidation in a trisodium phosphate bath, with the component to be checked being in the anode position;
8. Rinsing with cold water in a tank of running water;
9. Development by partial etching in a nitrohydrofluoric bath;
10. Rinsing with cold water as quickly and thoroughly as possible, followed by drying of the component; and
11. Reading the defects revealed, on the basis of shapes and colours (white, blut, grey-blue) which are peculiar to them.

However, this process does have some drawbacks. In particular, the existing products which are generally used for the chemical activation and are available in the trade are relatively costly, difficult to use, and deteriorate rapidly.

More particularly, when these commercially available products are used in conditions enabling between 0.8 and 1.3 μm of material to be removed in a 90- second immersion, i.e. with a concentration of 250 g/l, it is a drawback that between steps 5 and 6 of the process described above, i.e. between removal of the component from the chemical activation bath and immersion in the rinsing tank, sufficient time elapses for the etching reagent which is carried with the component and its support to continue acting, causing drainage marks. These marks will prevent, or at least limit, the reading of defects drawn in the same direction, such as fibrillation for example, their intensity being a function of the geometry of the component, the type of supporting structure used, and the aggressivity and the temperature of the bath. Moreover, the operative life of the bath is short at the prescribed rate, and there is no possibility of adding salt to compensate for exhaustion since it is close to saturation. In addition, temperature control is compulsory as the etching rate is multiplied by a factor of 1.5 or 2 for a 10° C. rise of bath temperature. Finally, on immersion of the components in the bath, the etching rate does not reach its maximum immediately, but only after a period termed the "depassivation period", which may last from 10 to 20 seconds. This depassivation time is not negligible in comparison with the immersion time of the components, i.e. about 1.5 minutes, and leads to systematic errors.

To overcome these various drawbacks, thought has been given to using a lower bath concentration of 120 to 150 g/l, with very frequent recharges of +30 to +60 g/l intended to maintain a certain degree of efficiency at the operating temperature. Unfortunately, while drainage marks are limited in this way and do not hinder the fault reading, the life of the bath is rather short and, in particular, quality assurance is very chancy. Indeed, the reaction rate is much too variable and prohibits the automation of the process, the thickness removed is small, depassivation time is too long, and the bath recharges are not very effective.

DESCRIPTION OF THE INVENTION

With the aim of overcoming the aforementioned drawbacks, according to the invention there is provided an acid etching bath for activating titanium alloys before macrographic anodic oxidation in an electro-chemical etching process comprising, in succession, the steps of degreasing, rinsing, activation by acid etching, rinsing, anodic oxidation in a trisodium phosphate bath, rinsing, and development by etching in a nitrohydrofluoric bath, said acid etching bath comprising, per liter, 75±5 ml of sulphuric acid ($H_2SO_4$) having a density of about 1.83, from 11 to 15 g of sodium fluoride (NaF), and water ($H_2O$) as the balance.

In use, the acid etching bath in accordance with the invention can be recharged when necessary, for example when the etching rate reaches the minimum acceptable rate of 0.60 μm/minute, by adding from 5 to 10 ml/1 of $H_2SO_4$ and from 3 to 4 g/1 of NaF to the bath.

With the new acid etching bath of the invention, not only is the quality of the macrographic etching excellent and drainage marks restricted, but there is also a definite improvement in quality assurance. Indeed, the bath life is long, and the etching rate, and hence the thickness removal, is constant, which permits automation of the process to be envisaged. Depassivation time can be taken into account in a precise manner, and the make-up amounts, in the quantities in accordance with the invention, are effective and moderate.

The bath composition in accordance with the invention is found to be particularly effective at a normal operating temperature between 16 and 25° C., which is easily obtained, even in a hot period, by agitation of the bath with compressed air.

Finally, the use of the bath in accordance with the invention is inexpensive compared with the existing, previously used baths.

We claim:

1. An acid etching bath comprising:
   (i) 75±5 ml/l of sulfuric acid (H$_2$SO$_4$) having a density of about 1.83;
   (ii) 11-15 g/l of sodium fluoride (NaF), and
   (iii) water.

2. An electro-chemical etching process for titanium alloy components comprising, in succession, the steps of:
   (i) degreasing;
   (ii) rinsing;
   (iii) activation by acid etching;
   (iv) rinsing;
   (v) anodic oxidation in a trisodium phosphate bath;
   (vi) rinsing; and
   (vii) development by etching in a nitrohydrofluoric bath,
   wherein said activation step is carried out in an acid etching bath comprising:
   (i) 75±5 ml/l of sulfuric acid (H$_2$SO$_4$) having a density of about 1.83;
   (ii) 11-15 g/l of sodium fluoride (NaF), and
   (iii) water;
   wherein said acid etching bath is periodically recharged by adding from 5 to 10 ml/l of sulfuric acid and from 3 to 4 g/l of sodium fluoride.

3. An electro-chemical etching process for titanium alloy components comprising, in succession, the steps of:
   (i) degreasing;
   (ii) rinsing;
   (iii) activation by acid etching;
   (iv) rinsing;
   (v) anodic oxidation in a trisodium phosphate bath;
   (vi) rinsing; and
   (vii) development by etching in a nitrohydrofluoric bath,
   wherein said activation step is carried out in an acid etching bath comprising:
   (i) 75±5 ml/l of sulfuric acid (H$_2$SO$_4$) having a density of about 1.83;
   (ii) 11-15 g/l of sodium fluoride (NaF), and
   (iii) water;
   at a temperature between 16°-25° C., and
   wherein said acid etching bath is agitated with compressed air.

4. A process according to claim 2, wherein said acid etching bath is recharged when the etching rate drops below 0.6 μm/minute.

* * * * *

UNITED STATES PATENT AND TRADEMARK OFFICE
CERTIFICATE OF CORRECTION

PATENT NO. : 5,209,829
DATED : May 11, 1993
INVENTOR(S) : Claude G.G. Gondel, et al It is certified that error appears in the above-indentified patent and that said Letters Patent is hereby corrected as shown below:

Column 1, line 52, "(white, blut, grey-blue)" should read —(white, blue, grey-blue)—.

Signed and Sealed this

Second Day of August, 1994

Attest:

BRUCE LEHMAN

Attesting Officer     Commissioner of Patents and Trademarks